(12) United States Patent
Abe et al.

(10) Patent No.: US 8,404,390 B2
(45) Date of Patent: Mar. 26, 2013

(54) NONAQUEOUS ELECTROLYTE SOLUTION FOR LITHIUM SECONDARY BATTERY AND LITHIUM SECONDARY BATTERY USING THE SAME

(75) Inventors: Koji Abe, Ube (JP); Kazuhiro Miyoshi, Ube (JP); Yoshihiro Ushigoe, Ube (JP); Manabu Takase, Ube (JP); Kazuyuki Kawabe, Ube (JP)

(73) Assignee: Ube Industries, Ltd., Ube-shi (JP)

( * ) Notice: Subject to any disclaimer, the term of this patent is extended or adjusted under 35 U.S.C. 154(b) by 660 days.

(21) Appl. No.: 12/596,300

(22) PCT Filed: Apr. 15, 2008

(86) PCT No.: PCT/JP2008/057350
§ 371 (c)(1),
(2), (4) Date: Oct. 16, 2009

(87) PCT Pub. No.: WO2008/133112
PCT Pub. Date: Nov. 6, 2008

(65) Prior Publication Data
US 2010/0092872 A1    Apr. 15, 2010

(30) Foreign Application Priority Data

Apr. 20, 2007 (JP) .................. 2007-112400
Oct. 25, 2007 (JP) .................. 2007-277364
Dec. 28, 2007 (JP) .................. 2007-338405

(51) Int. Cl.
H01M 6/16 (2006.01)
(52) U.S. Cl. ........ 429/340; 429/341; 429/330; 429/332; 429/331; 429/231.1; 429/231.95; 429/231.8; 252/62.2
(58) Field of Classification Search ............ 429/340, 429/341, 330, 332, 331, 231.1, 231.95, 231.8; 252/62.2
See application file for complete search history.

(56) References Cited

U.S. PATENT DOCUMENTS

2002/0015894 A1  2/2002  Wariishi et al.
2004/0197667 A1  10/2004  Noh et al.

FOREIGN PATENT DOCUMENTS

| JP | 6 96770    | 4/1994  |
| JP | 2000 21446 | 1/2000  |
| JP | 2005 108440| 4/2005  |
| JP | 2006 294519| 10/2006 |
| JP | 2007-173147| * 7/2007 |
| JP | 2007 173147| 7/2007  |

OTHER PUBLICATIONS

Skatteboel, Lars et al., "Thiopyran 1,1-Dioxide Derivatives from Addition of Amines to Propargyl Sulfone", The Journal of Organic Chemistry, vol. 33, No. 2, pp. 548-552, Feb. 1968.

* cited by examiner

Primary Examiner — Laura Weiner
(74) Attorney, Agent, or Firm — Oblon, Spivak, McClelland, Maier & Neustadt, L.L.P.

(57) ABSTRACT

The present invention provides (1) a sulfone compounds having a propargyl group, (2) a nonaqueous electrolytic solution for lithium secondary batteries, which comprises an electrolyte salt dissolved in a nonaqueous solvent and contains a sulfone compound having a specific structure that has an $SO_2$ group with a propargyl group or a vinyl group bonding thereto, in an amount of from 0.01 to 10% by weight of the nonaqueous electrolytic solution, and which can prevent gas generation and is excellent in battery characteristics such as cycle property and the like, and (3) a lithium secondary battery comprising a positive electrode, a negative electrode and a nonaqueous electrolytic solution of an electrolyte salt dissolved in a nonaqueous solvent, wherein the nonaqueous electrolytic solution contains a sulfone compound having a specific structure, in an amount of from 0.01 to 10% by weight of the nonaqueous electrolytic solution.

13 Claims, No Drawings

NONAQUEOUS ELECTROLYTE SOLUTION FOR LITHIUM SECONDARY BATTERY AND LITHIUM SECONDARY BATTERY USING THE SAME

TECHNICAL FIELD

The present invention relates to a sulfone compound useful as intermediate materials for medicines, agricultural chemicals, electronic materials, polymer materials and the like, or as battery materials, as well as to a nonaqueous electrolytic solution comprising it for lithium secondary batteries, which can prevent vapor generation in use of batteries at high voltage and which is excellent in battery characteristics such as cycle property and the like, and also to a lithium secondary battery using it.

BACKGROUND ART

In recent years, lithium secondary batteries have been widely used as driving power supplies for small electronic devices such as mobile telephones, notebook-size personal computers and the like, and also as power supplies for electric vehicles and for electric power storage.

A lithium secondary battery is mainly constituted of a positive electrode and a negative electrode containing a material capable of absorbing and releasing lithium, and a nonaqueous electrolytic solution containing a lithium salt. A carbonate such as ethylene carbonate (EC), propylene carbonate (PC) or the like is used as the nonaqueous electrolytic solution.

As the negative electrode for the lithium secondary battery, known are metal lithium, and metal compounds (simple metal substances, oxides, alloys with lithium, etc.) and carbon materials capable of absorbing and releasing lithium. In particular, nonaqueous electrolytic solution secondary batteries using carbon materials capable of absorbing and releasing lithium, for example, coke, graphite (artificial graphite, natural graphite) or the like of those carbon materials have been widely put into practical use.

The above-mentioned negative electrode materials store and release lithium and electron at a low potential on the same level as that of lithium metal, and therefore especially at high temperatures, they have a possibility of reduction and decomposition of many solvents, and irrespective of the type of the negative electrode material, the solvent in the electrolytic solution may be partly reduced and decomposed on a negative electrode, therefore bringing about some problems in that the resistance may increase owing to deposition of decomposed products, that the battery may be swollen owing to gas generation through solvent decomposition and that lithium ion movement may be retarded thereby worsening the battery characteristics such as cycle property and the like.

On the other hand, a material capable of storing and releasing lithium such as $LiCoO_2$, $LiMn_2O_4$, $LiNiO_2$, $LiFePO_4$ or the like that is used as a positive electrode material stores and releases lithium and electron at a high voltage of 3.5 V or more based on lithium, and therefore has a possibility of oxidation and decomposition of many solvents; and irrespective of the type of the positive electrode material, the solvent in the electrolytic solution may be partly oxidized and decomposed on a positive electrode, therefore bringing about some problems in that the resistance may increase owing to deposition of decomposed products, that the battery may be swollen owing to gas generation through solvent decomposition and that lithium ion movement may be retarded thereby worsening the battery characteristics such as cycle property and the like.

Given that the situation, electronic appliances equipped with lithium secondary batteries therein expands the range of functions and they are in a stream of further increase in the power consumption. With that, the capacity of lithium secondary batteries is being much increased, and the space volume for the nonaqueous electrolytic solution in the battery is decreased by increasing the density of the electrode and by reducing the useless space volume in the battery. Accordingly, the situation is that even decomposition of only a small amount of the nonaqueous electrolytic solution may worsen the battery performance at high temperatures and the battery may swell. Further, the battery service condition is that the capacity is increased by further elevating the charge voltage, in which, therefore, the electrolytic solution is more readily decomposed.

In particular, the gas generation, if any, not only worsens the cycle property and the storage property but also brings about further troubles in that the batteries, as swollen, could not be housed in a limited battery housing space and also problems in that the safety mechanism for current shutdown or the like may be turned on thereby to make the batteries out of service.

Accordingly, an electrolytic solution is longed for, capable of realizing a battery that has a high capacity and is free from degradation of cycle property and storage property and is not swollen even at high temperatures.

Patent Reference 1 discloses a lithium secondary battery using a nonaqueous electrolytic solution to which are added a carbonate additive such as 4-fluoro-1,3-dioxolan-2-one or the like and an organic sulfonic compound such as divinyl sulfone.

Patent Reference 2 discloses a lithium secondary battery provided with a nonaqueous electrolytic solution containing a halogen atom-containing cyclic carbonate such as 4-fluoro-1,3-dioxolan-2-one or the like and a sulfur-containing compound.

Patent Reference 3 discloses a nonaqueous electrolytic solution secondary battery using a nonaqueous electrolytic solution to which is added a sulfone compound such as bis(allylsulfonyl)methane or the like.

[Patent Reference 1] JP-A 2005-108440
[Patent Reference 2] JP-A 2006-294519
[Patent Reference 3] JP-A 2007-173147

DISCLOSURE OF THE INVENTION

Problems that the Invention is to Solve

An object of the present invention is to provide a nonaqueous electrolytic solution for lithium secondary batteries, capable of preventing gas generation in use of batteries at high voltage and excellent in battery characteristics such as cycle property and the like, and to provide a lithium secondary battery using it.

Means for Solving the Problems

The present inventors have studied in detail the performance of the above-mentioned prior-art nonaqueous electrolytic solutions. As a result, the nonaqueous electrolytic solution in Patent Reference 1 is not satisfactory in point of the effect of preventing gas generation, and requires further improvements in the cycle property thereof.

Patent Reference 2 discloses dimethyl sulfone (with two alkyl groups bonding to the $SO_2$ group) and diphenyl sulfone (with conjugated double bond-having phenyl groups bonding to the $SO_2$ group) as concrete examples of the sulfur-containing compound; however, even though the nonaqueous electrolytic solution containing the compound is used, the cycle property at high temperatures is not still satisfactory, and the gas generation-preventing effect in use at high temperatures is insufficient.

The nonaqueous electrolytic solution in Patent Reference 3 is insufficient in point of the high-temperature cycle property thereof and of the gas generation-preventing effect in use of full-charged batteries at high temperatures.

The inventors have further made assiduous studies to solve the above-mentioned problems, and have found that, when a specific amount of a sulfone compound that has a specific structure having an $SO_2$ group with a propargyl group or a vinyl group bonding thereto is added to a nonaqueous electrolytic solution, then the cycle property of the lithium secondary battery using the electrolytic solution is excellent and, even in use at high temperatures thereof, the battery brings about little gas generation, and have completed the present invention.

Specifically, the present invention provides the following (1) to (3):

(1) A sulfone compound represented by the following general formula (I):

[Formula 1]

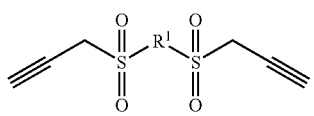

(wherein $R^1$ represents a divalent linking group having from 2 to 6 carbon atoms and containing at least one ether bond).

(2) A nonaqueous electrolytic solution for lithium secondary batteries, comprising an electrolyte salt dissolved in a nonaqueous solvent and containing bis(2-propynyl)sulfone and/or a sulfone compound represented by the following general formula (II) in an amount of from 0.01 to 10% by mass of the nonaqueous electrolytic solution:

[Formula 2]

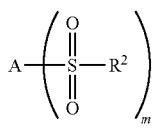

(wherein $R^2$ represents a 2-propynyl group or a vinyl group; m indicates 2 or 3; A represents a divalent linking group having from 1 to 5 carbon atoms and optionally containing an ether bond when m is 2, but when m is 3, A represents a trivalent linking group composed of carbon and hydrogen atoms and having from 1 to 5 carbon atoms).

(3) A lithium secondary battery comprising a positive electrode, a negative electrode and a nonaqueous electrolytic solution of an electrolyte salt dissolved in a nonaqueous solvent, wherein the nonaqueous electrolytic solution contains bis(2-propynyl)sulfone and/or a sulfone compound of the above-mentioned general formula (II) in an amount of from 0.01 to 10% by mass of the nonaqueous electrolytic solution.

Effect of the Invention

According to the present invention, there are provided (1) a sulfone compound useful as a battery material, etc.; (2) a nonaqueous electrolytic solution for lithium secondary batteries, capable of preventing gas generation in use of batteries at high voltage and excellent in battery characteristics such as cycle property, etc.; and (3) a lithium secondary battery using it.

BEST MODE FOR CARRYING OUT THE INVENTION

The nonaqueous electrolytic solution for lithium secondary batteries containing a sulfone compound of the present invention, and the lithium secondary battery using it are described in detail hereinunder.

[Nonaqueous Electrolytic Solution]

The nonaqueous electrolytic solution of the present invention is a nonaqueous electrolytic solution of an electrolyte salt dissolved in a nonaqueous solvent, which contains a sulfone compound having a specific structure that has an $SO_2$ group with a propargyl group or a vinyl group bonding thereto, in an amount of from 0.01 to 10% by mass of the nonaqueous electrolytic solution.

[Sulfone Compound Represented by General Formula (I)]

The sulfone compound represented by the following general formula (I) of the present invention is a novel compound.

[Formula 3]

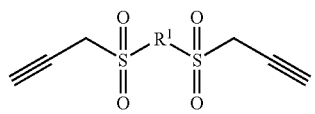

(wherein $R^1$ represents a divalent linking group having from 2 to 6 carbon atoms and containing at least one ether bond).

The sulfone compound represented by the general formula (I) concretely includes compounds where $R^1$ is $—CH_2OCH_2—$, $—C_2H_4OC_2H_4—$, or $—C_2H_4OC_2H_4OC_2H_4—$, etc. In this, the number of the ether bonds is preferably from 1 to 3, more preferably one, as the compound is more effective for bettering the high-temperature cycle property and for preventing gas generation.

The alkylene groups on both sides of the ether oxygen may be asymmetric or symmetric, but are preferably symmetric. The alkylene groups on both sides of the ether oxygen may be branched.

Concrete sulfone compounds represented by the above-mentioned general formula (I) include bis[(2-propinylsulfonyl)methyl]ether, 2,2'-bis[(2-propinylsulfonyl)ethyl]ether (this compound may also be referred to as bis[2-(2-propinylsulfonyl)ethyl]ether), 3,3'-bis[(2-propinylsulfonyl)propyl]ether (this compound may also be referred to as bis[3-(2-propinylsulfonyl)propyl]ether), ethylene glycol 2,2'-bis[(2-propinylsulfonyl)ethyl]ether (this compound may also be referred to as ethylene glycol bis[2-(2-propinylsulfonyl)ethyl]ether), etc.; and preferred is 2,2'-bis[(2-propinylsulfonyl)ethyl]ether.

The production method for the sulfone compound represented by the general formula (I) of the present invention is not specifically defined. For example, a dithiol having from 2 to 6 carbon atoms and containing at least one ether bond is reacted with an alkali metal in a solvent or in the absence of a solvent to give a thiolate, then this is reacted with a propargyl halide to give a sulfide intermediate; and after optionally purified, the intermediate is oxidized to give the intended compound.

[Bis(2-propynyl)sulfone and/or Sulfone Compound Represented by General Formula (II)]

The sulfone compound to be added to the nonaqueous electrolytic solution of the present invention is bis(2-propynyl)sulfone and/or a compound represented by the following general formula (II):

[Formula 4]

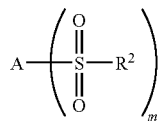

(II)

(wherein $R^2$ represents a 2-propynyl group or a vinyl group; m indicates 2 or 3; A represents a divalent linking group having from 1 to 5 carbon atoms and optionally containing an ether bond when m is 2, but when m is 3, A represents a trivalent linking group composed of carbon and hydrogen atoms and having from 1 to 5 carbon atoms).

In the general formula (II), specific examples of the divalent linking group A when m is 2 include linear or branched alkylene groups (alkanediyl groups) having from 1 to 6 carbon atoms, preferably linear alkylene groups (alkanediyl groups) having from 1 to 4 carbon atoms, such as a methylene group, an ethylene group, a propylene group (propane-1,2-diyl group), various types of butylene groups, various types of pentylene groups, etc.; and ether bond-having groups such as —CH$_2$OCH$_2$—, —C$_2$H$_4$OC$_2$H$_4$—, —C$_2$H$_4$OC$_2$H$_4$OC$_2$H$_4$—, etc.

Specific examples of the sulfone compound having a divalent linking group A represented by the above-mentioned formula (II) include sulfone compounds having an alkylene group, such as bis(2-propynylsulfonyl)methane, 1,2-bis(2-propynylsulfonyl)ethane, 1,1-bis(2-propynylsulfonyl)ethane, 1,2-bis(2-propynylsulfonyl)propane, 1,3-bis(2-propynylsulfonyl)propane, 2,2-bis(2-propynylsulfonyl)propane, 1,3-bis(2-propynylsulfonyl)butane, 1,4-bis(2-propynylsulfonyl)butane, 1,5-bis(2-propynylsulfonyl)pentane, 1,6-bis(2-propynylsulfonyl)hexane, bis(vinylsulfonyl)methane, 1,2-bis(vinylsulfonyl)ethane, 1,1-bis(vinylsulfonyl)ethane, 1,2-bis(vinylsulfonyl)propane, 1,3-bis(vinylsulfonyl)propane, 2,2-bis(vinylsulfonyl)propane, 1,3-bis(vinylsulfonyl)butane, 1,4-bis(vinylsulfonyl)butane, 1,5-bis(vinylsulfonyl)pentane, 1,6-bis(vinylsulfonyl)hexane, etc.; or sulfone compounds having an ether bond, such as bis(2-propynylsulfonylmethyl)ether, 2,2'-bis(2-propynylsulfonylethyl)ether (this compound may also be referred to as 2,2'-bis[(2-propynylsulfonyl)ethyl]ether), 3,3'-bis(2-propynylsulfonylpropyl)ether, ethylene glycol 2,2'-bis(2-propynylsulfonylethyl)ether, bis(vinylsulfonylmethyl)ether, bis(vinylsulfonylethyl)ether (this compound may also be referred to as bis(2-vinylsulfonylethyl)ether), bis(vinylsulfonylpropyl)ether (this compound may also be referred to as bis(3-vinylsulfonylpropyl)ether), ethylene glycol bis(vinylsulfonylethyl)ether (this compound may also be referred to as ethylene glycol bis(2-vinylsulfonylethyl)ether), etc.

Of the above-mentioned compounds, preferred are bis(2-propynyl)sulfone, 1,2-bis(2-propynylsulfonyl)ethane, 1,3-bis(2-propynylsulfonyl)propane, 2,2'-bis(2-propynylsulfonylethyl)ether, bis(vinylsulfonyl)methane, 1,2-bis(vinylsulfonyl)ethane, 1,4-bis(vinylsulfonyl)butane and bis(2-vinylsulfonylethyl)ether, as more effective for bettering the high-temperature cycle property and for preventing gas generation.

In the general formula (II), specific examples of the trivalent linking group A when m is 3 include the following:

[Formula 5]

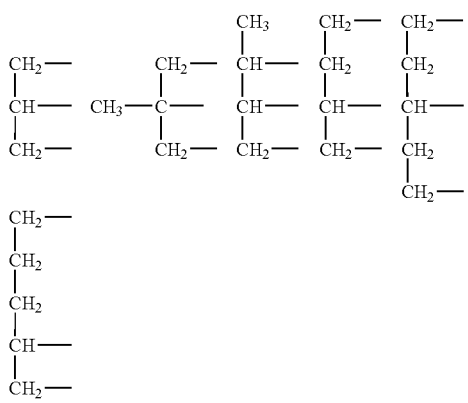

Specific examples of the sulfone compound having a trivalent linking group A represented by the above-mentioned formula (II) include sulfone compounds having an alkylene group, such as 1,2,3-tris(2-propynylsulfonyl)propane, 2-methyl-1,2,3-tris(2-propynylsulfonyl)propane, 1,2,3-tris(2-propynylsulfonyl)butane, 1,2,4-tris(2-propynylsulfonyl)butane, 1,2,5-tris(2-propynylsulfonyl)pentane, 1,3,5-tris(2-propynylsulfonyl)pentane, 1,2,3-tris(vinylsulfonyl)propane, 2-methyl-1,2,3-tris(vinylsulfonyl)propane, 1,2,3-tris(vinylsulfonyl)butane, 1,2,4-tris(vinylsulfonyl)butane, 1,2,5-tris(vinylsulfonyl)pentane, 1,3,5-tris(vinylsulfonyl)pentane, etc. Of those, preferred are 1,2,3-tris(2-propynylsulfonyl)propane, 1,2,4-tris(2-propynylsulfonyl)butane and 1,2,3-tris(vinylsulfonyl)propane, as more effective for bettering the high-temperature cycle property and for preventing gas generation.

[Sulfone Compound Represented by General Formula (III)]

Specific examples of the sulfone compound represented by the general formula (II), which is added to the nonaqueous electrolytic solution of the present invention, include compounds of the following general formula (III):

[Formula 6]

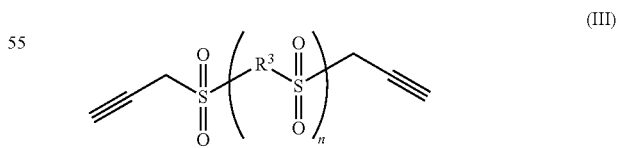

(III)

(wherein $R^3$ represents a linear or branched alkylene group having from 1 to 6 carbon atoms, or a divalent linking group having from 2 to 6 carbon atoms and containing at least one ether bond: n indicates 0 or 1).

Concrete embodiments of the sulfone compound represented by the above-mentioned general formula (III) are shown below.

In the general formula (III), n is 0 or 1; and when n is 0, the compound is bis(2-propynyl)sulfone.

When n is 1, the linear or branched alkylene group having from 1 to 6 carbon atoms for $R^3$ includes a methylene group, an ethylene group, an ethylidene group (branched), a trimethylene group, a propane-1,2-diyl group (branched), a propylidene group (branched), a tetramethylene group, a butane-1,3-diyl group (branched), a 2-methylpropane-1,2-diyl group (branched), a butylidene group (branched), a 1,5-pentylene group, a 1,6-hexylene group, etc. Of those, preferred is a linear alkylene groups having from 1 to 4 carbon atoms such as a methylene group, an ethylene group, a trimethylene group or a tetramethylene group, as the compound is more effective for bettering the high-temperature cycle property and for preventing gas generation.

In case where $R^3$ is a divalent linking group having from 2 to 6 carbon atoms and containing at least one ether bond (this is the same as the general formula (I)), the sulfone compound may exhibit its effect of bettering the high-temperature cycle property and preventing gas generation in a broad range of the amount of the compound to be added, and therefore this is more favorable as readily controlling the amount of the compound to be added. Concrete examples of the group include —$CH_2OCH_2$—, —$C_2H_4OC_2H_4$—, —$C_2H_4OC_2H_4OC_2H_4$—, etc. In this, the number of the ether bonds is preferably from 1 to 3, more preferably one, as the compound is more effective for bettering the high-temperature cycle property and for preventing gas generation.

The alkylene groups on both sides of the ether oxygen may be asymmetric or symmetric, but are preferably symmetric. The alkylene groups on both sides of the ether oxygen may be branched.

[Sulfone Compound Represented by General Formula (IV)]

Specific examples of the sulfone compound represented by the general formula (II), which is added to the nonaqueous electrolytic solution of the present invention, include compounds of the following general formula (IV):

[Formula 7]

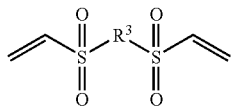

(IV)

(wherein $R^3$ is the same as above).

In the general formula (IV), the linear or branched alkylene group having from 1 to 6 carbon atoms, and the divalent linking group having from 2 to 6 carbon atoms and containing at least one ether bond for $R^3$ are the same as those exemplified for $R^3$ in the general formula (III), and their preferred embodiments are also the same; and therefore their concrete description is herein omitted.

[Content of the Sulfone Compound Represented by General Formulae (II) to (IV)]

In the nonaqueous electrolytic solution of the present invention, when the content of bis(2-propynyl)sulfone and/or the sulfone compound represented by the general formula (II) (including the sulfone compound represented by the general formulae (III) and (IV)—the same shall apply hereinunder) is more than 10% by mass, then the surface film formation on the electrode may be too much and the high-temperature cycle property may be thereby worsened; however, when the content is less than 0.01% by mass, then the surface film formation may be insufficient and the compound may be ineffective for bettering the high-temperature cycle property and for preventing gas generation. Accordingly, the content of the compound is preferably 0.01% by mass or more of the nonaqueous electrolytic solution, more preferably 0.1% by mass or more, even more preferably 0.2% by mass or more, still more preferably 0.3% by mass or more. The uppermost limit of the content is 10% by mass or less, preferably 7% by mass or less, even more preferably 5% by mass or less, still more preferably 3% by mass or less.

Though not always clear, the reason why the high-temperature cycle property can be improved and the gas generation can be prevented by the addition of bis(2-propynyl) sulfone and/or the sulfone compound represented by the general formula (II) may be considered as follows: Since the 2-propynyl group-having sulfone compound in the present invention has a structure with a triple bond bonding thereto via the carbon adjacent to the $SO_2$ group, the polymerization at the triple bond site thereof readily goes on, starting from the active carbon adjacent to the strongly electron-withdrawing $SO_2$ group; and on the other hand, the vinyl group-having sulfone compound in the present invention readily polymerizes since the vinyl group directly bonds to the $SO_2$ group. In addition, since the compound has two 2-propynyl groups bonding thereto via the $SO_2$ group, or has two or more structures each with a 2-propynyl group or a vinyl group directly bonding to the $SO_2$ group (2-propynylsulfonyl groups or vinylsulfonyl groups) via a specific linking group therebetween, its polymerization goes on isotropically, therefore producing a dense surface film.

In the nonaqueous electrolytic solution of the present invention, bis(2-propynyl)sulfone and/or the sulfone compound represented by the general formula (II) may attain the effect of bettering the high-temperature cycle property and preventing gas generation even when they are singly in the solution; however, when combined with a nonaqueous solvent, an electrolyte salt and further, some other additives to be mentioned below, the compound may exhibit a specific effect of synergistically more bettering the high-temperature cycle property and preventing gas generation. Though not always clear as yet at present, the reason may be considered as follows: The constitutive elements of these nonaqueous solvent, electrolyte salt and additives may be caught in the dense surface film formed from the sulfone compound in the present invention, therefore producing a denser surface film.

[Nonaqueous Solvent]

The nonaqueous solvent to be used in the nonaqueous electrolytic solution of the present invention includes cyclic carbonates, linear carbonates, linear esters, ethers, amides, phosphates, sulfones, lactones, nitriles, S=O bond-containing compounds, etc.

The cyclic carbonates include ethylene carbonate (EC), propylene carbonate (PC), butylene carbonate (BC), 4-fluoro-1,3-dioxolan-2-one (FEC), trans or cis-4,5-difluoro-1,3-dioxolan-2-one (hereinafter the two are referred to as a generic term "DFEC"), vinylene carbonate (VC), vinylethylene carbonate (VEC), etc. Of those cyclic carbonates, preferred for use herein is at least one selected from EC, PC, VC, FEC and DFEC having a high dielectric constant as capable of increasing the electroconductivity of the electrolytic solution; and more preferred is using VC or FEC as capable of bettering the cycle property. In particular, at least one cyclic carbonate selected from EC, PC and VC is preferred for use herein, as capable of further reducing gas generation.

In general, when an electrolytic solution contains FEC, DFEC, VC or VEC, then the gas generation from it may increase; however, the nonaqueous electrolytic solution containing a sulfone compound of the present invention can prevent gas generation.

One type of these solvents may be used singly; however, use of two or more types thereof as combined is favorable as more effective for bettering the high-temperature cycle property and for preventing gas generation. More preferably, three or more types of the solvents are used as combined. Preferred combinations of these cyclic carbonates include EC and PC, FEC and PC, EC and VC, FEC and VC, PC and VC, EC and PC and VC, FEC and PC and VC, FEC and EC and PC and VC, etc.

Not specifically defined, the content of the cyclic carbonate is preferably within a range of from 10 to 40% by volume, based on the overall volume of the nonaqueous solvent. When the content is less than 10% by volume, then the electroconductivity of the electrolytic solution may lower and the cycle property may worsen; but when the content is more than 40% by volume, then the high-temperature cycle property may worsen and the gas generation may increase. In particular, it is more desirable that PC is in the electrolytic solution in an amount of from 5 to 10% by volume as capable of bettering the high-temperature cycle property and reducing gas generation.

The linear carbonates include asymmetric linear carbonates such as methyl ethyl carbonate (MEC), methyl propyl carbonate, methyl isopropyl carbonate, methyl butyl carbonate, ethyl propyl carbonate, etc.; and symmetric linear carbonates such as dimethyl carbonate (DMC), diethyl carbonate (DEC), dipropyl carbonate, dibutyl carbonate, etc. Especially preferably, the electrolytic solution contains an asymmetric carbonate, as capable of bettering the high-temperature cycle property and reducing gas generation.

One type of these linear carbonates may be used singly; however, use of two or more types thereof as combined is favorable as more effective for bettering the cycle property and for reducing gas generation.

Not specifically defined, the content of the linear carbonate is preferably within a range of from 60 to 90% by volume, based on the overall volume of the nonaqueous solvent. When the content is less than 60% by volume, then the viscosity of the electrolytic solution may increase and therefore the high-temperature cycle property may worsen and the gas generation may increase. On the other hand, when the content is more than 90% by volume, then the electroconductivity of the electrolytic solution may lower and the high-temperature cycle property may worsen. Accordingly, the content is preferably within the above-mentioned range.

When a linear ester such methyl propionate, methyl pivalate, butyl pivalate, hexyl pivalate, octyl pivalate, dimethyl oxalate, ethyl methyl oxalate, diethyl oxalate or the like, or an ether such as tetrahydrofuran, 2-methyltetrahydrofuran, 1,3-dioxane, 1,4-dioxane, 1,2-dimethoxyethane, 1,2-diethoxyethane, 1,2-dibutoxyethane or the like; or an amide such as dimethylformamide or the like; or a phosphate such as trimethyl phosphate, tributyl phosphate, trioctyl phosphate or the like is added, then the viscosity of the nonaqueous electrolytic solution may be lowered, and the battery characteristics such as the output property and the cycle property can be bettered. When a sulfone such as sulfolane or the like, or a lactone such as γ-butyrolactone, γ-valerolactone, α-angelicalactone or the like is added, then the nonaqueous electrolytic solution may be made retardant to flames; and when a nitrile such as acetonitrile, succinonitrile, adiponitrile or the like is added, then the storage property tends to be bettered.

The S=O bond-containing compounds include 1,3-propanesultone (PS), ethylene sulfite, 1,2-cyclohexanediol cyclic sulfite, 5-vinyl-hexahydro-1,3,2-benzodioxathiol-2-oxide, 1,4-butanediol dimethanesulfonate, 1,3-butanediol dimethanesulfonate, divinyl sulfone, etc.

Use of the above-mentioned S=O bond-containing compounds, as combined, is favorable, as capable of more effectively reducing gas generation and bettering the cycle property. However, when the content of the S=O bond-containing compound is more than 10% by mass, then it may worsen the cycle property or could not bring about the effect of preventing gas generation; but when the content is less than 0.01% by mass, then it could not bring about the effect of bettering the high-temperature cycle property and preventing gas generation. Accordingly, the content is preferably 0.01% by mass or more of the nonaqueous electrolytic solution, more preferably 0.1% by mass or more, most preferably 0.5% by mass or more. Its uppermost limit is preferably 10 by mass or less, more preferably 5% by mass or less, most preferably 3% by mass or less.

In general, the above-mentioned nonaqueous solvents are mixed for use herein, for the purpose of attaining the suitable properties of the solution. The combinations include, for example, a combination of cyclic carbonates and linear carbonates, a combination of cyclic carbonates and linear carbonates and lactones, a combination of cyclic carbonates and linear carbonates and ethers, a combination of cyclic carbonates and linear carbonates and linear esters, a combination of cyclic carbonates and linear carbonates and nitriles, a combination of cyclic carbonates and linear carbonates and S=O bond-containing compounds, etc.

Of those, preferred is a nonaqueous solvent of a combination of at least cyclic carbonates and linear carbonates, as more effective for bettering the high-temperature cycle property and for preventing gas generation. More concretely, preferred is a combination of at least one cyclic carbonate selected from EC, PC, VC and FEC, and at least one linear carbonate selected from DMC, MEC and DEC.

The blend ratio of the cyclic carbonates and the linear carbonates is not specifically defined. From the viewpoint of bettering the cycle property and retarding gas generation, the ratio of cyclic carbonate/linear carbonate (by volume) is preferably from 10/90 to 40/60, more preferably from 10/90 to 30/70, even more preferably from 15/85 to 25/75, still more preferably from 15/85 to 35/65, most preferably from 20/80 to 30/70.

[Electrolyte Salt]

The electrolyte salt for use in the present invention includes Li salts such as $LiPF_6$, $LiBF_4$, $LiClO_4$, etc.; linear fluoroalkyl group-having lithium salts such as $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$, etc.; cyclic fluoroalkylene chain-having lithium salts such as $(CF_2)_2(SO_2)_2NLi$, $(CF_2)_3(SO_2)_2NLi$, etc.; and lithium salts with an anion of an oxalate complex such as lithium bis[oxalate-O,O']borate, lithium difluoro[oxalate-O,O']borate, etc. Of those, especially preferred electrolyte salts are $LiPF_6$, $LiBF_4$, $LiN(SO_2CF_3)_2$, $LiN(SO_2C_2F_5)_2$. One or more of these electrolyte salts may be used herein either singly or as combined.

A preferred combination of these electrolyte salts is a combination containing $LiPF_6$ as combined with at least one selected from $LiBF_4$, $LiN(SO_2CF_3)_2$ and $LiN(SO_2C_2F_5)_2$. Preferred are a combination of $LiPF_6$ and $LiBF_4$; a combination of $LiPF_6$ and $LiN(SO_2CF_3)_2$; a combination of $LiPF_6$ and $LiN(SO_2C_2F_5)_2$, etc. When the ratio (by mol) of $LiPF_6$/[$LiBF_4$ or $LiN(SO_2CF_3)_2$ or $LiN(SO_2C_2F_5)_2$] is smaller than 70/30 in point of the proportion of $LiPF_6$, or when the ratio is larger than 99/1 in point of the proportion of $LiPF_6$, then the cycle property may worsen. Accordingly, the ratio (by mol) of $LiPF_6/[LiBF_4$ or $LiN(SO_2CF_3)_2$ or $LiN(SO_2C_2F_5)_2]$ is preferably within a range of from 70/30 to 99/1, more preferably from 80/20 to 98/2. The combination falling within the above range is more effective for bettering the high-temperature cycle property and for preventing gas generation.

The electrolyte salts may be combined in any desired ratio. In the combination of $LiPF_6$ with any of $LiBF_4$, $LiN(SO_2CF_3)_2$ and $LiN(SO_2C_2F_5)_2$, when the proportion (as ratio by mol) of the other electrolyte salt than those ingredients to the total electrolyte salts is less than 0.01%, then the high-temperature storage stability of the electrolyte mixture may be poor; but when it is more than 45%, then the high-temperature storage stability thereof may worsen. Accordingly, the proportion (as ratio by mol) is preferably from 0.01 to 45%, more preferably from 0.03 to 20%, even more preferably from 0.05 to 10%, most preferably from 0.05 to 5%.

The concentration of all these electrolyte salts as dissolved in the solution is generally preferably 0.3 M or more relative to the above-mentioned nonaqueous solvent, more preferably 0.5 M or more, most preferably 0.7 M or more. The uppermost limit of the concentration is preferably 2.5 M or less, more preferably 2.0 M or less, even more preferably 1.5 M or less, most preferably 1.2 M or less.

[Other Additives]

An aromatic compound may be added to the nonaqueous electrolytic solution of the present invention, thereby securing the safety of the battery in overcharging. Preferred examples of the aromatic compound include cyclohexylbenzene, fluorocyclohexylbenzene compound (1-fluoro-2-cyclohexylbenzene, 1-fluoro-3-cyclohexylbenzene, 1-fluoro-4-cyclohexylbenzene), tert-butylbenzene, tert-amylbenzene, 1-fluoro-4-tert-butylbenzene, 1,3-di-tert-butylbenzene, biphenyl, terphenyl (o-, m-, p-form), diphenyl ether, fluorobenzene, difluorobenzene (o-, m-, p-form), 2,4-difluoroanisole, partially hydrogenated terphenyls (1,2-dicyclohexylbenzene, 2-phenylbicyclohexyl, 1,2-diphenylcyclohexane, o-cyclohexylbiphenyl), etc.

Preferably, the aromatic compound is added to the nonaqueous electrolytic solution in an amount of from 0.1 to 10% by mass of the solution. One or more of these aromatic compounds may be used either singly or as combined.

[Production of Nonaqueous Electrolytic Solution]

The nonaqueous electrolytic solution of the present invention can be produced, for example, by mixing the above-mentioned nonaqueous solvents followed by dissolving therein the above-mentioned electrolyte salt and a sulfone compound represented by the above-mentioned general formulae (II) to (IV) in an amount of from 0.01 to 10% by mass of the resulting nonaqueous electrolytic solution.

In this case, the compounds to be added to the nonaqueous solvent and the electrolytic solution are preferably previously purified within a range not significantly detracting from the producibility, in which, therefore, the impurity content is preferably as low as possible.

For example, air or carbon dioxide may be incorporated into the nonaqueous electrolytic solution of the present invention to thereby prevent gas generation resulting from decomposition of electrolytic solution and to enhance the battery characteristics such as the long-term cycle property and the charge storage property.

In the present invention, from the viewpoint of enhancing charging and discharging characteristics at high temperatures, the nonaqueous electrolytic solution preferably contains carbon dioxide as dissolved therein. The amount of carbon dioxide to be dissolved in the nonaqueous electrolytic solution is preferably 0.001% by mass or more of the solution, more preferably 0.05% by mass or more, even more preferably 0.2% by mass or more; and most preferably, carbon dioxide is dissolved in the nonaqueous electrolytic solution until its saturation therein.

[Lithium Secondary Battery]

The lithium secondary battery of the present invention comprises a positive electrode, a negative electrode and the above-mentioned nonaqueous electrolytic solution of an electrolyte salt dissolved in a nonaqueous solvent. The other constitutive components such as a positive electrode and a negative electrode except for the nonaqueous electrolytic solution can be used with no limitation.

For example, as the positive electrode active material, usable are complex metal oxides of lithium containing any of cobalt, manganese or nickel. One or more such positive electrode active materials may be used either singly or as combined.

The complex metal oxides include, for example, $LiCoO_2$, $LiMn_2O_4$, $LiNiO_2$, $LiCo_{1-x}Ni_xO_2$ (0.01<x<1), $LiCo_{1/3}Ni_{1/3}Mn_{1/3}O_2$, $LiNi_{1/2}Mn_{3/2}O_4$, $LiCo_{0.98}Mg_{0.02}O_2$, etc. Combinations of $LiCoO_2$ and $LiMn_2O_4$; $LiCoO_2$ and $LiNiO_2$; $LiMn_2O_4$ and $LiNiO_2$ are acceptable herein.

The lithium complex oxide may be partly substituted with any other element to enhance the safety in overcharging or the cycle property and to enable the use of the battery at a charging potential of 4.3 V or more. For example, a part of cobalt, manganese and nickel may be substituted with at least one element of Sn, Mg, Fe, Ti, Al, Zr, Cr, V, Ga, Zn, Cu, Bi, Mo, La, etc.; or O may be partly substituted with S or F; or the oxide may be coated with a compound containing such other element.

Of those, preferred are lithium complex metal oxides such as $LiCoO_2$, $LiMn_2O_4$ and $LiNiO_2$, with which the positive electrode charging potential in a full-charging state may be 4.3 V or more with reference to Li. More preferred are lithium complex oxides usable at 4.4 V or more, such as $LiCo_{1-x}M_xO_2$ (where M is at least one element of Sn, Mg, Fe, Ti, Al, Zr, Cr, V, Ga, Zn and Cu; $0.001 \leq x \leq 0.05$), $LiCo_{1/3}Ni_{1/3}Mn_{1/3}O_2$, and $LiNi_{1/2}Mn_{3/2}O_4$. When a lithium/transition metal complex oxide having a high charging potential is used, then gas may be generated through reaction with electrolytic solution in charging; however, the lithium secondary battery of the present invention can prevent such gas generation.

Further, lithium-containing olivine-type phosphates are also usable as the positive electrode active material. Their concrete examples include $LiFePO_4$, $LiCoPO_4$, $LiNiPO_4$, $LiMnPO_4$, etc.

The lithium-containing olivine-type phosphates may be partly substituted with any other element. For example, apart of iron, cobalt, nickel and manganese therein may be substituted with at least one element selected from Co, Mn, Ni, Mg, Al, B, Ti, V, Nb, Cu, Zn, Mo, Ca, Sr, W and Zr; or the phosphates may be coated with a compound or a carbon material containing any of these other elements. Of those, preferred are $LiFePO_4$ and $LiCoPO_4$.

The lithium-containing olivine-type phosphate may be combined with, for example, the above-mentioned positive electrode active material.

Not specifically defined, the electroconductive agent of the positive electrode may be any electron-transmitting material not undergoing chemical change. For example, it includes graphites such as natural graphite (flaky graphite, etc.), artificial graphite, etc.; carbon blacks such as acetylene black, Ketjen black, channel black, furnace black, lamp black, thermal black, etc. Graphites and carbon blacks may be combined suitably. The amount of the electroconductive agent to be added to the positive electrode mixture is preferably from 1 to 10% by mass, more preferably from 2 to 5% by mass.

The positive electrode may be formed by mixing the above-mentioned positive electrode active material with an electroconductive agent such as acetylene black, carbon black or the like, and with a binder such as polytetrafluoroethylene (PTFE), polyvinylidene fluoride (PVDF), styrene/butadiene copolymer (SBR), acrylonitrile/butadiene copolymer (NBR), carboxymethyl cellulose (CMC), ethylene/propylene/diene terpolymer or the like, then adding thereto a high-boiling point solvent such as 1-methyl-2-pyrrolidone or the like, and kneading them to give a positive electrode mixture, thereafter applying the positive electrode mixture onto an aluminium foil or a stainless lath plate or the like serving as a collector, and drying and shaping it under pressure, and then heat-treating it in vacuum at a temperature of from 50° C. to 250° C. or so for about 2 hours.

The density of the part except the collector of the positive electrode may be generally 1.5 g/cm$^3$ or more, and for further increasing the capacity of the battery, the density is preferably 2 g/cm$^3$ or more, more preferably 3 g/cm$^3$ or more, even more preferably 3.6 g/cm$^3$ or more.

As the negative electrode active material, usable are one or more of lithium metal, lithium alloys, and carbon materials and metal compounds capable of absorbing and releasing lithium, either singly or as combined.

Of those, preferred are high-crystalline carbon materials such as artificial graphite, natural graphite or the like of which the ability of absorbing and releasing lithium ions is good. More preferred is a carbon material having a graphite-type crystal structure where the lattice (002) spacing ($d_{002}$) is at most 0.340 nm (nanometers), especially from 0.335 to 0.337 nm. More preferably, the high-crystalline carbon material is coated with a low-crystalline carbon material, as capable of more effectively preventing gas generation. When a high-crystalline carbon material is used, then it may react with an electrolytic solution in charging thereby worsening the high-temperature cycle property and reducing gas generation; however, in the lithium secondary battery of the present invention, the reaction with the nonaqueous electrolytic solution can be retarded.

The metal compound capable of absorbing and releasing lithium, serving as a negative electrode active material, includes compounds containing at least one metal element of Si, Ge, Sn, Pb, P, Sb, Bi, Al, Ga, In, Ti, Mn, Fe, Co, Ni, Cu, Zn, Ag, Mg, Sr, Ba, etc. These metal compounds may have any morphology of simple substances, alloys, oxides, nitrides, sulfides, borides, alloys with lithium or the like; but preferred are any of simple substances, alloys, oxides and alloys with lithium, as capable of increasing the battery capacity. Above all, more preferred are those containing at least one element selected from Si, Ge and Sn, and even more preferred are those containing at least one element selected from Si and Sn, as capable of increasing the capacity of the battery.

The negative electrode may be formed, using the same electroconductive agent, binder and high-boiling point solvent as in the formation of the above-mentioned positive electrode. These are mixed and kneaded to give a negative electrode mixture, then the negative electrode mixture is applied onto a copper foil or the like serving as a collector, then dried and shaped under pressure, and thereafter heat-treated in vacuum at a temperature of from 50° C. to 250° C. or so for about 2 hours.

In case where graphite is used as the negative electrode active material, the density of the part except the collector of the negative electrode may be generally 1.4 g/cm$^3$ or more, and for further increasing the capacity of the battery, the density is preferably 1.6 g/cm$^3$ or more, more preferably 1.7 g/cm$^3$ or more.

The structure of the lithium secondary battery is not specifically defined. The secondary battery may be a coin-shaped battery, a cylindrical battery, a square-shaped battery, or a laminate-type battery, each having a single layered or multi-layered separator.

The battery separator may be composed of a single layered or laminated porous film, woven fabric, or non-woven fabric of a polyolefin such as polypropylene, polyethylene, etc.

The lithium secondary battery of the present invention exhibits excellent long-term cycle property even when the final charging voltage is 4.2 V or more and particularly 4.3 V or more. Furthermore, the cycle property is good and the gas generation can be prevented even when the final charging voltage is 4.4 V. The final discharging voltage can be set to generally 2.8 V or more and further 2.5 V or more; however, for the lithium secondary battery of the present invention, the voltage may be set to 2.0 V or more. Although the current value is not restricted, a constant current discharge of from 0.1 to 3 C is generally employed. The lithium secondary battery of the present invention may be charged and discharged at −40° C. to 100° C. and preferably at 0° C. to 80° C.

In general, because of its structural factor, a square-shaped battery, a laminate-type battery or the like may readily swell through gas generation therein; however, the lithium secondary battery comprising the nonaqueous electrolytic solution of the present invention can be prevented from swelling through gas generation.

In the present invention, as a countermeasure against an increase in internal pressure of the lithium secondary battery, there may be employed a method of providing a safety valve in the battery cap or a method of forming a cutout in the battery component such as the battery can, the gasket or the like. In addition, as a safety countermeasure against overcharging, a current breaker capable of detecting the internal pressure of the battery to cut off the current may be provided in the battery cap. The lithium secondary battery using the nonaqueous electrolytic solution of the present invention generates little gas, and is therefore free from a trouble of battery breakdown owing to the above-mentioned mechanisms acting at high voltage or high temperature

EXAMPLES

Production Example for the sulfone compound of the present invention, and Examples of using the electrolytic solution of the present invention are given below.

Production Example

Production of 2,2'-bis[(2-propynylsulfonyl)ethyl]ether

A mixture liquid of 15.0 g (109 mmol) of bis(2-mercaptoethyl)ether and 24 g of methanol was dropwise added to 44.0 g (228 mmol) of 28% sodium methoxide/methanol solution with cooling in an ice bath, at an internal temperature not higher than 10° C. The ice bath was taken off, and at 25° C., this was kept stirred for 1 hour as a slurry, and then the reaction liquid was again cooled in an ice bath. Then, 54.8 g (228 mmol) of propargyl bromide was dropwise added thereto, and stirred at 25° C. for 30 minutes. After the reaction, the reaction liquid was poured into saturated brine, then the organic layer was extracted out with ethyl acetate, and the organic layer was dried with MgSO$_4$ and concentrated to give 21.8 g (102 mmol) of 2,2'-bis[(2-propynylthio)ethyl]ether (yield, 94%). The resulting 2,2'-bis[(2-propynylthio)ethyl] ether was transferred into a reactor equipped with a reflux condenser, then dissolved in 60 g of water and 15 g of methanol, and then 0.20 g (1.02 mmol) of phosphoric acid and 0.34 g (1.02 mmol) of sodium tungstate were added thereto. The reaction liquid was cooled to 20° C., and 49.0 g (408 mmol) of 30% hydrogen peroxide water was dropwise added thereto. After the addition, this was further stirred for 1 hour, then washed with water in the same manner as above, and concentrated to give 30.1 g of 2,2'-bis[(2-propynylsulfonyl)ethyl] ether (yield 82%).

In the battery test, one prepared by purifying the obtained 2,2'-bis[(2-propynylsulfonyl)ethyl]ether through silica gel chromatography (eluent: ethyl acetate/methanol=15/1) was used.

The structure of the obtained 2,2'-bis[(2-propynylsulfonyl) ethyl]ether was confirmed through $^1$H-NMR and $^{13}$C-NMR (using JEOL's Model AL300) and through mass spectrometry (using Hitachi's Model M80B).

(1) $^1$H-NMR (300 MHz, $d_6$-DMSO): δ=4.26 (d, J=2.93 Hz, 4H), 3.82 (t, J=5.61 Hz, 4H), 3.51 (t, J=2.69 Hz, 2H), 3.50 (t, J=5.61 Hz, 4H).

(2) $^{13}$C-NMR (75 MHz, $d_6$-DMSO): δ=78.1, 72.6, 63.9, 51.3, 45.8.

(3) mass spectrometry: MS (EI) m/z (%)=278 (4) [M$^+$], 239 (10), 211 (7), 175 (4), 131 (28), 103 (12), 67 (20), 39 (100).

Examples I-1 to I-4

Preparation of Nonaqueous Electrolytic Solution

LiPF$_6$ to be 1 M was dissolved in a nonaqueous solvent of EC/MEC=30/70 (ratio by volume), and further bis(2-propynyl) sulfone was added thereto to prepare a nonaqueous electrolytic solution, in an amount of 0.1% by mass of the resulting nonaqueous electrolytic solution (Example I-1), 1% by mass (Example I-2), 5% by mass (Example I-3) and 10% by mass (Example I-4).

[Production of Lithium Ion Secondary Battery]

94% by mass of LiCo$_{1/3}$Ni$_{1/3}$Mn$_{1/3}$O$_2$ (positive electrode active material) and 3% by mass of acetylene black (electroconductive agent) were mixed, and added to and mixed with a solution previously prepared by dissolving 3% by mass of polyvinylidene fluoride (binder) in 1-methyl-2-pyrrolidone, thereby preparing a positive electrode mixture paste. The positive electrode mixture paste was applied onto both surfaces of an aluminium foil (collector), dried, processed under pressure and cut into a predetermined size, thereby producing a long rectangular, positive electrode sheet. The density of a part of the positive electrode except the collector was 3.6 g/cm$^3$. 95% by mass of artificial graphite coated with low crystalline carbon ($d_{002}$=0.335 nm, negative electrode active material) was added to and mixed with a solution previously prepared by dissolving 5% by mass of polyvinylidene fluoride (binder) in 1-methyl-2-pyrrolidone, thereby preparing a negative electrode mixture paste. The negative electrode mixture paste was applied onto both surfaces of a copper foil (collector), dried, processed under pressure and cut into a predetermined size, thereby producing a long rectangular, negative electrode sheet. The density of a part of the negative electrode except the collector was 1.7 g/cm$^3$. The positive electrode sheet, a porous polyethylene film separator, the negative electrode sheet and a separator were laminated in that order, and the resulting laminate was coiled up. The coil was housed into a nickel-plated, iron-made cylindrical battery can serving also as a negative electrode terminal. Further, the nonaqueous electrolytic solution was injected thereinto, and the can was calked with a battery cap having a positive electrode terminal, via a gasket therebetween, thereby constructing a 18650-type cylindrical battery. The positive electrode terminal was connected to the positive electrode sheet via an aluminium lead tab therebetween; and the negative electrode can was previously connected to the negative electrode sheet inside the battery, via a nickel lead tab therebetween.

[Evaluation of Cycle Property]

In a thermostat chamber kept at 60° C., the battery constructed according to the above-mentioned method was charged up to a final voltage of 4.2 V for 3 hours with a constant current of 1 C and a constant voltage, and then this was discharged under a constant current of 1 C to a discharge voltage of 3.0 V. This is one cycle. The battery was subjected to 100 cycles. After 100 cycles, the discharge capacity retention of the battery was determined according to the following formula, and was 74%.

Discharge Capacity Retention(%)=(discharge capacity in 100 cycles/discharge capacity in 1 cycle)×100.

[Determination of Gas Generation]

An electrolytic solution having the same composition as above was injected into a different cylindrical battery, the battery was put in a thermostat chamber kept at 25° C., and charged up to a final voltage of 4.3 V for 7 hours with a constant current of 0.2 C and a constant voltage, and then this was put into a thermostat chamber at 80° C., stored therein for 3 days while kept in an open circuit state, and thereafter the gas generation was measured according to an Archimedes method. The gas generation was 75%, based on the gas generation, 100% in Comparative Example I-1.

The condition in constructing the batteries and the battery characteristics are shown in Table I-1.

Examples I-5 and I-6

Cylindrical batteries were produced in the same manner as in Example I-1, for which, however, LiPF$_6$ to be 1 M was dissolved in a nonaqueous solvent of EC/MEC=15/85 (ratio by volume) (Example I-5) or EC/MEC=40/60 (ratio by volume) (Example I-6), and further, bis(2-propynyl)sulfone was added thereto to prepare a nonaqueous electrolytic solution, in an amount of 1% by mass of the resulting nonaqueous electrolytic solution; and the batteries were evaluated. The results are shown in Table I-1.

Example I-7

A cylindrical battery was produced in the same manner as in Example I-1, for which, however, LiPF$_6$ to be 0.95 M and LiN(SO$_2$CF$_3$)$_2$ [in Table 1, this is abbreviated as LiTFSI] to be 0.05M were dissolved in a nonaqueous solvent of EC/PC/VC/MEC/DEC=23/5/2/50/20 (ratio by volume), and further, bis(2-propynyl) sulfone was added thereto to prepare a nonaqueous electrolytic solution, in an amount of 1% by mass of the resulting nonaqueous electrolytic solution; and the battery was evaluated. The results are shown in Table I-1.

Example I-8

A cylindrical battery was produced in the same manner as in Example I-1, for which, however, LiPF$_6$ to be 0.95 M and LiBF$_4$ to be 0.05 M were dissolved in a nonaqueous solvent of FEC/PC/MEC=20/10/70 (ratio by volume), and further, bis (2-propynyl) sulfone was added thereto to prepare a nonaqueous electrolytic solution, in an amount of 1% by mass of the resulting nonaqueous electrolytic solution; and the battery was evaluated. The results are shown in Table I-1.

Examples I-9 and I-10

Cylindrical batteries were produced in the same manner as in Example I-1, for which, however, $LiPF_6$ to be 1 M was dissolved in a nonaqueous solvent of EC/MEC=30/70 (ratio by volume), and further, 1,2-bis(2-propynylsulfonyl)ethane (Example I-9) or 2,2'-bis[(2-propynylsulfonyl)ethyl]ether (Example I-10) was added thereto to prepare a nonaqueous electrolytic solution, in an amount of 1% by mass of the resulting nonaqueous electrolytic solution; and the batteries were evaluated. The results are shown in Table I-1.

Comparative Example I-1

A cylindrical battery was produced in the same manner as in Example I-1, for which, however, $LiPF_6$ to be 1 M was dissolved in a nonaqueous solvent of EC/MEC=30/70 (ratio by volume), but bis(2-propynyl)sulfone was not added to the nonaqueous electrolytic solution; and the battery was evaluated. The results are shown in Table I-1.

Comparative Examples I-2 to I-4

Cylindrical batteries were produced in the same manner as in Example I-1, for which, however, $LiPF_6$ to be 1 M was dissolved in a nonaqueous solvent of EC/MEC=30/70 (ratio by volume), and further, dimethyl sulfone (Comparative Example I-2), diphenyl sulfone (Comparative Example I-3) or bis(allylsulfonyl)methane (Comparative Example I-4) was added in place of adding bis(2-propynyl)sulfone thereto to prepare a nonaqueous electrolytic solution, in an amount of 1% by mass of the resulting nonaqueous electrolytic solution; and the batteries were evaluated. The results are shown in Table I-1.

Example I-11

A negative electrode sheet was produced, using Si (negative electrode active material) in place of the negative electrode active material used in Example I-2. 80% by mass of Si and 15% by mass of acetylene black (electroconductive agent) were mixed, and added to and mixed with a solution previously prepared by dissolving 5% by mass of polyvinylidene fluoride (binder) in 1-methyl-2-pyrrolidone, thereby preparing a negative electrode mixture paste. A cylindrical battery was produced in the same manner as in Example I-2, for which, however, the negative electrode mixture paste was applied onto a copper foil (collector), dried, processed under pressure and cut into a predetermined size, thereby producing a long rectangular, negative electrode sheet; and the battery was evaluated. The results are shown Table I-2. The gas generation is a value computed based on the gas generation, 100% in Comparative Example I-5.

Comparative Example I-5

A cylindrical battery was produced in the same manner as in Example I-11, for which, however, bis(2-propynyl)sulfone was not added to the nonaqueous electrolytic solution; and the battery was evaluated. The results are shown Table I-2.

TABLE I-1

| | Composition of Electrolyte Salt Composition of Nonaqueous Solvent (ratio by volume) | Sulfone Compound Type | Amount Added (% by mass) | Discharge Capacity Retention after 100 cycles (%) | Gas Generation (%) |
|---|---|---|---|---|---|
| Example I-1 | 1M LiPF6 EC/MEC (30/70) | bis(2-propynyl) sulfone | 0.1 | 74 | 75 |
| Example I-2 | 1M LiPF6 EC/MEC (30/70) | bis(2-propynyl) sulfone | 1 | 81 | 67 |
| Example I-3 | 1M LiPF6 EC/MEC (30/70) | bis(2-propynyl) sulfone | 5 | 80 | 68 |
| Example I-4 | 1M LiPF6 EC/MEC (30/70) | bis(2-propynyl) sulfone | 10 | 78 | 69 |
| Example I-5 | 1M LiPF6 EC/MEC (15/85) | bis(2-propynyl) sulfone | 1 | 79 | 65 |
| Example I-6 | 1M LiPF6 EC/MEC (40/60) | bis(2-propynyl) sulfone | 1 | 76 | 71 |
| Example I-7 | 0.95M LiPF6 + 0.05M LiTFSI EC/PC/VC/MEC/DEC (23/5/2/50/20) | bis(2-propynyl) sulfone | 1 | 85 | 63 |
| Example I-8 | 0.95M LiPF6 + 0.05M LiBF4 FEC/PC/MEC (20/10/70) | bis(2-propynyl) sulfone | 1 | 82 | 70 |
| Example I-9 | 1M LiPF6 EC/MEC (30/70) | 1,2-(bis-2-propynylsulfonyl)-ethane | 1 | 82 | 65 |
| Example I-10 | 1M LiPF6 EC/MEC (30/70) | 2,2'-bis[(2-propynylsulfonyl)ethyl] ether | 1 | 83 | 64 |
| Comparative Example I-1 | 1M LiPF6 EC/MEC (30/70) | none | — | 57 | 100 |
| Comparative Example I-2 | 1M LiPF6 EC/MEC (30/70) | dimethyl sulfone | 1 | 61 | 96 |
| Comparative Example I-3 | 1M LiPF6 EC/MEC (30/70) | diphenyl sulfone | 1 | 63 | 92 |
| Comparative Example I-4 | 1M LiPF6 EC/MEC (30/70) | bis(allylsulfonyl)methane | 1 | 65 | 89 |

TABLE I-2

| | Composition of Electrolyte Salt Composition of Nonaqueous Solvent (ratio by volume) | Sulfone Compound | | Discharge Capacity | |
|---|---|---|---|---|---|
| | | Type | Amount Added (% by mass) | Retention after 100 cycles (%) | Gas Generation (%) |
| Example I-11 | 1M LiPF6 EC/MEC (30/70) | bis(2-propynyl) sulfone | 1 | 61 | 61 |
| Comparative Example I-5 | 1M LiPF6 EC/MEC (30/70) | bis(2-propynyl) sulfone | — | 22 | 100 |

Example I-12

A positive electrode sheet was produced, using LiFePO$_4$ (positive electrode active material) in place of the positive electrode active material used in Example I-2. 90% by mass of LiFePO$_4$ and 5% by mass of acetylene black (electroconductive agent) were mixed, and added to and mixed with a solution previously prepared by dissolving 5% by mass of polyvinylidene fluoride (binder) in 1-methyl-2-pyrrolidone, thereby preparing a positive electrode mixture paste. A cylindrical battery was produced and evaluated in the same manner as in Example I-2, for which, however, the positive electrode mixture paste was applied onto an aluminium foil (collector), dried, processed under pressure and cut into a predetermined size, thereby producing a long rectangular, positive electrode sheet, and the final charging voltage was 3.6 V and the final discharging voltage was 2.0 V in evaluation of the cycle property and in determination of the gas generation level. The results are shown in Table I-3. The gas generation is a value computed based on the gas generation, 100% in Comparative Example I-6.

Comparative Example I-6

A cylindrical battery was produced in the same manner as in Example I-12, for which, however, bis(2-propynyl)sulfone was not added to the nonaqueous electrolytic solution; and the battery was evaluated. The results are shown Table I-3.

TABLE I-3

| | Composition of Electrolyte Salt Composition of Nonaqueous Solvent (ratio by volume) | Sulfone Compound | | Discharge Capacity | |
|---|---|---|---|---|---|
| | | Type | Amount Added (% by mass) | Retention after 100 cycles (%) | Gas Generation (%) |
| Example I-12 | 1 M LiPF6 EC/MEC (30/70) | bis(2-propynyl) sulfone | 1 | 83 | 63 |
| Comparative Example I-6 | 1 M LiPF6 EC/MEC (30/70) | bis(2-propynyl) sulfone | — | 69 | 100 |

The lithium secondary batteries of Examples I-1 to I-10 are all noticeably improved in point of the high-temperature cycle property and the gas generation-preventing effect thereof, as compared with the lithium secondary batteries in Comparative Example I-1 where the sulfone compound of the present invention was not added, Comparative Example I-2 where dimethyl sulfone having a structure of two methyl groups, a type of alkyl groups, bonding to the SO$_2$ group was added, Comparative Example I-3 where diphenyl sulfone having a structure of two phenyl groups with a conjugated double bond, bonding to the SO$_2$ group was added, and Comparative Example I-4 where bis(allylsulfonyl)methane having a structure of two allyl groups with a double bond, bonding to the SO$_2$ group was added. Accordingly, it is known that, when a sulfone compound where two structures each having a triple bond via the carbon adjacent to the SO$_2$ group bond to the linking group having the SO$_2$ group is added to a nonaqueous electrolytic solution of an electrolyte salt dissolved in a nonaqueous solvent, then it brings about unexpected specific effects.

From comparison between Example I-11 and Comparative Example I-5, and comparison between Example I-12 and Comparative Example I-6, the case where Si is used as the negative electrode, and the case where a lithium-containing olivine-type iron phosphate is used as the positive electrode also exhibit the same effects. Accordingly, it is obvious that the effects of the present invention do not depend on a specific positive electrode or negative electrode.

Example II-1

Preparation of Electrolytic Solution

LiPF$_6$ to be 0.95 M and LiN(SO$_2$CF$_3$)$_2$ [this is abbreviated as LiTFSI in Table II) to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)= 23/5/2/50/20, and further, 1,2-bis(vinylsulfonyl)ethane was added thereto to prepare a nonaqueous electrolytic solution, in an amount of 0.1% by mass of the resulting nonaqueous electrolytic solution.

[Production of Lithium Ion Secondary Battery]

92% by mass of LiCoO$_2$ (positive electrode active material), 3% by mass of acetylene black (electroconductive agent) and 5% by mass of polyvinylidene fluoride (binder) were mixed, and added to and mixed with a solvent of 1-methyl-2-pyrrolidone. This was applied onto an aluminium foil collector, dried, processed under pressure and cut into a predetermined size, thereby producing a long rectangular, positive electrode sheet. 95% by mass of artificial graphite (negative electrode active material) and 5% by mass of polyvinylidene fluoride (binder) were mixed, to which was added a solvent of 1-methyl-2-pyrrolidone. This was applied onto a copper foil collector, dried, processed under pressure and cut into a predetermined size, thereby producing a long rectangular, negative electrode sheet. The positive electrode sheet, a porous polyethylene film separator, the negative electrode sheet and a separator were laminated in that order, and this was coiled up. The coil was housed into a nickel-plated, iron-made cylindrical battery can serving also as a negative electrode terminal. Further, the electrolytic solution was injected thereinto, and the can was calked with a battery cap having a positive electrode terminal, via a gasket therebetween, thereby constructing a cylindrical battery. The positive electrode terminal was connected to the positive electrode sheet via an aluminium lead tab therebetween; and the negative electrode can was previously connected to the negative electrode sheet inside the battery, via a nickel lead tab therebetween.

[Evaluation of Cycle Property]

In a thermostat chamber kept at 45° C., the battery constructed according to the above-mentioned method was charged up to a final voltage of 4.3 V for 3 hours with a constant current of 1 C and a constant voltage, and then this was discharged under a constant current of 1 C to a discharge voltage of 2.7 V. This is one cycle. The battery was subjected to 100 cycles. After 100 cycles, the discharge capacity retention of the battery was determined according to the following formula, and was 85%.

Discharge Capacity Retention(%)=(discharge capacity in 100 cycles/discharge capacity in 1 cycle)×100.

[Determination of Gas Generation]

An electrolytic solution having the same composition as above was injected into a different cylindrical battery, the battery was put in a thermostat chamber kept at 25° C., and charged up to a final voltage of 4.3 V for 7 hours with a constant current of 0.2 C and a constant voltage, and then this was put into a thermostat chamber at 60° C., and charged at a constant voltage of 4.3 V for 3 days, and thereafter the gas generation was measured according to an Archimedes process. The gas generation was 65%, based on the gas generation, 100% in Comparative Example II-1.

The condition in constructing the batteries and the battery characteristics are shown in Table II-1.

Examples II-2 to II-4

Cylindrical batteries were produced in the same manner as in Example II-1, for which, however, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=23/5/2/50/20, and further, 1,2-bis(vinylsulfonyl)ethane was added thereto to prepare a nonaqueous electrolytic solution, in an amount of 1% by mass, 5% by mass or 10% by mass of the resulting nonaqueous electrolytic solution; and the batteries were tested for the battery characteristics and the gas generation level. The results are shown in Table II-1.

Example II-5

A cylindrical battery was produced in the same manner as in Example II-1, for which, however, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=8/5/2/65/20, and further, 1,2-bis(vinylsulfonyl)ethane was added thereto to prepare a nonaqueous electrolytic solution, in an amount of 1% by mass of the resulting nonaqueous electrolytic solution; and the battery was tested for the battery characteristics and the gas generation level. The results are shown in Table II-1.

Example II-6

A cylindrical battery was produced in the same manner as in Example II-1, for which, however, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=33/5/2/40/20, and further, 1,2-bis(vinylsulfonyl)ethane was added thereto to prepare a nonaqueous electrolytic solution, in an amount of 1% by mass of the resulting nonaqueous electrolytic solution; and the battery was tested for the battery characteristics and the gas generation level. The results are shown in Table II-1.

Example II-7

A cylindrical battery was produced in the same manner as in Example II-1, for which, however, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=23/5/2/50/20, and further, bis(vinylsulfonyl)methane was added thereto to prepare a nonaqueous electrolytic solution, in an amount of 1% by mass of the resulting nonaqueous electrolytic solution; and the battery was tested for the battery characteristics and the gas generation level. The results are shown in Table II-1.

Example II-8

A cylindrical battery was produced in the same manner as in Example II-1, for which, however, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=23/5/2/50/20, and further, 1,4-bis(vinylsulfonyl)butane was added thereto to prepare a nonaqueous electrolytic solution, in an amount of 1% by mass of the resulting nonaqueous electrolytic solution; and the battery was tested for the battery characteristics and the gas generation level. The results are shown in Table II-1.

Example II-9

A cylindrical battery was produced in the same manner as in Example II-1, for which, however, LiPF$_6$ to be 0.95 M and LiBF$_4$ to be 0.05 M were dissolved in a nonaqueous solvent of 4-fluoro-1,3-dioxolan-2-one (FFC)/propylene carbonate (PC)/methyl ethyl carbonate (MEC)/dimethyl carbonate (DMC) (ratio by volume)=20/10/50/20, and further, 1,2-bis(vinylsulfonyl)ethane was added thereto to prepare a nonaqueous electrolytic solution, in an amount of 1% by mass of the resulting nonaqueous electrolytic solution; and the battery was tested for the battery characteristics and the gas generation level. The results are shown in Table II-1.

Comparative Example II-1

A cylindrical battery was produced in the same manner as in Example II-1, for which, however, LiPF$_6$ to be 0.95 M and $LiN(SO_2CF_3)_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=23/5/2/50/20, but 1,2-bis(vinylsulfonyl)ethane was not added to the nonaqueous electrolytic solution; and the battery was tested for the battery characteristics and the gas generation level. The results are shown in Table II-1.

Comparative Example II-2

A cylindrical battery was produced in the same manner as in Example II-1, for which, however, $LiPF_6$ to be 0.95 M and $LiBF_4$ to be 0.05 M were dissolved in a nonaqueous solvent of 4-fluoro-1,3-dioxolan-2-one (FFC)/propylene carbonate (PC)/methyl ethyl carbonate (MEC)/dimethyl carbonate (DMC) (ratio by volume)=20/10/50/20, and further, divinyl sulfone was added thereto to prepare a nonaqueous electrolytic solution, in an amount of 1% by mass of the resulting nonaqueous electrolytic solution; and the battery was tested for the battery characteristics and the gas generation level. The results are shown in Table II-1.

Comparative Example II-3

A cylindrical battery was produced in the same manner as in Example II-1, for which, however, $LiPF_6$ to be 0.95 M and $LiN(SO_2CF_3)_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=23/5/2/50/20, and further 1,2-bis(methylsulfonyl)ethane was added thereto to prepare a nonaqueous electrolytic solution, in an amount of 1% by mass of the resulting nonaqueous electrolytic solution; and the battery was tested for the battery characteristics and the gas generation level. The results are shown in Table II-1.

Examples II-10 to II-14

Cylindrical batteries were produced in the same manner as in Example II-1, for which, however, $LiPF_6$ to be 1 M was dissolved in a nonaqueous solvent of ethylene carbonate (EC)/methyl ethyl carbonate (MEC)/diethyl carbonate (DEC) (ratio by volume)=30/50/20, and further, bis(2-vinylsulfonylethyl)ether was added thereto to prepare a nonaqueous electrolytic solution, in an amount of 0.1% by mass, 1% by mass, 2% by mass, 5% by mass or 10% by mass of the resulting nonaqueous electrolytic solution; and the batteries were tested for the battery characteristics and the gas generation level. The results are shown in Table II-2.

Example II-15

A cylindrical battery was produced in the same manner as in Example II-1, for which, however, $LiPF_6$ to be 1 M was dissolved in a nonaqueous solvent of ethylene carbonate (EC)/methyl ethyl carbonate (MEC)/diethyl carbonate (DEC) (ratio by volume)=30/50/20, and further, bis(2-vinylsulfonylethyl)ether was added thereto to prepare a nonaqueous electrolytic solution, in an amount of 1% by mass, and ethylene sulfite thereto in an amount of 0.5% by mass of the resulting nonaqueous electrolytic solution; and the battery was tested for the battery characteristics and the gas generation level. The results are shown in Table II-2.

Example II-16

A cylindrical battery was produced in the same manner as in Example II-1, for which, however, $LiPF_6$ to be 1 M was dissolved in a nonaqueous solvent of ethylene carbonate (EC)/methyl ethyl carbonate (MEC)/diethyl carbonate (DEC) (ratio by volume)=30/50/20, and further, bis(2-vinylsulfonylethyl)ether was added thereto to prepare a nonaqueous electrolytic solution, in an amount of 1% by mass, and 1,3-propanesultone thereto in an amount of 2% by mass of the resulting nonaqueous electrolytic solution; and the battery was tested for the battery characteristics and the gas generation level. The results are shown in Table II-2.

TABLE II-1

| | Composition of Electrolyte Salt Composition of Nonaqueous Solvent (ratio by volume) | Sulfone Compound Type | Amount Added (% by mass) | Discharge Capacity Retention after 100 cycles (%) | Gas Generation (%) |
|---|---|---|---|---|---|
| Example II-1 | 0.95M LiPF6 + 0.05M LiTFSI EC/PC/VC/MEC/DEC (23/5/2/50/20) | 1,2-bis(vinylsulfonyl)ethane | 0.1 | 85 | 65 |
| Example II-2 | 0.95M LiPF6 + 0.05M LiTFSI EC/PC/VC/MEC/DEC (23/5/2/50/20) | 1,2-bis(vinylsulfonyl)ethane | 1 | 90 | 59 |
| Example II-3 | 0.95M LiPF6 + 0.05M LiTFSI EC/PC/VC/MEC/DEC (23/5/2/50/20) | 1,2-bis(vinylsulfonyl)ethane | 5 | 89 | 60 |
| Example II-4 | 0.95M LiPF6 + 0.05M LiTFSI EC/PC/VC/MEC/DEC (23/5/2/50/20) | 1,2-bis(vinylsulfonyl)ethane | 10 | 87 | 63 |
| Example II-5 | 0.95M LiPF6 + 0.05M LiTFSI EC/PC/VC/MEC/DEC (8/5/2/65/20) | 1,2-bis(vinylsulfonyl)ethane | 1 | 89 | 56 |
| Example II-6 | 0.95M LiPF6 + 0.05M LiTFSI EC/PC/VC/MEC/DEC (33/5/2/40/20) | 1,2-bis(vinylsulfonyl)ethane | 1 | 86 | 67 |
| Example II-7 | 0.95M LiPF6 + 0.05M LiTFSI EC/PC/VC/MEC/DEC (23/5/2/50/20) | bis(vinylsulfonyl)methane | 1 | 88 | 62 |
| Example II-8 | 0.95M LiPF6 + 0.05M LiTFSI EC/PC/VC/MEC/DEC (23/5/2/50/20) | 1,4-bis(vinylsulfonyl)butane | 1 | 81 | 70 |
| Example II-9 | 0.95M LiPF6 + 0.05M LiBF4 FEC/PC/MEC/DMC (20/10/50/20) | 1,2-bis(vinylsulfonyl)ethane | 1 | 80 | 82 |
| Comparative Example II-1 | 0.95M LiPF6 + 0.05M LiTFSI EC/PC/VC/MEC/DEC (23/5/2/50/20) | none | — | 67 | 100 |
| Comparative Example II-2 | 0.95M LiPF6 + 0.05M LiBF4 FEC/PC/MEC/DMC (20/10/50/20) | divinyl sulfone | 1 | 72 | 89 |
| Comparative Example II-3 | 0.95M LiPF6 + 0.05M LiTFSI EC/PC/VC/MEC/DEC (23/5/2/50/20) | 1,2-bis(methylsulfonyl)ethane | 1 | 70 | 98 |

Example II-17

A cylindrical battery was produced in the same manner as in Example II-1, for which, however, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=23/5/2/50/20, and further, bis(2-vinylsulfonylethyl)ether was added thereto to prepare a nonaqueous electrolytic solution, in an amount of 1% by mass of the resulting nonaqueous electrolytic solution; and the battery was tested for the battery characteristics and the gas generation level. The results are shown in Table II-2.

Example II-18

A cylindrical battery was produced in the same manner as in Example II-1, for which, however, LiPF$_6$ to be 0.95 M and LiBF$_4$ to be 0.05 M were dissolved in a nonaqueous solvent of 4-fluoro-1,3-dioxolan-2-one (FEC)/propylene carbonate (PC)/methyl ethyl carbonate (MEC)/diethyl carbonate (DEC) (ratio by volume)=20/10/50/20, and further, bis(2-vinylsulfonylethyl)ether was added thereto to prepare a nonaqueous electrolytic solution, in an amount of 1% by mass of the resulting nonaqueous electrolytic solution; and the battery was tested for the battery characteristics and the gas generation level. The results are shown in Table II-2.

Comparative Example II-4

A cylindrical battery was produced in the same manner as in Example II-1, for which, however, LiPF$_6$ to be 1 M was dissolved in a nonaqueous solvent of ethylene carbonate (EC)/methyl ethyl carbonate (MEC)/diethyl carbonate (DEC) (ratio by volume)=30/50/20, but 1,2-bis(vinylsulfonyl)ethane was not added to the nonaqueous electrolytic solution; and the battery was tested for the battery characteristics and the gas generation level. The results are shown in Table II-2.

Example II-19

A cylindrical battery was produced in the same manner as in Example II-1 except for the following: Si was used as the negative electrode active material in place of artificial graphite. 75% by mass of Si (negative electrode active material), 10% by mass of artificial graphite (electroconductive agent), 10% by mass of acetylene black (electroconductive agent) and 5% by mass of polyvinylidene fluoride (binder) were mixed, to which was added a solvent of 1-methyl-2-pyrrolidone. The resulting mixture was applied onto a copper foil collector, dried, processed under pressure and cut into a predetermined size, thereby producing a long rectangular, negative electrode sheet. LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=23/5/2/50/20, and further 1,2-bis(vinylsulfonyl)ethane was added thereto to prepare a nonaqueous electrolytic solution, in an amount of 1% by mass of the resulting nonaqueous electrolytic solution. Thus produced, the battery was tested for the battery characteristics and the gas generation level. The results are shown in Table II-3.

Example II-20

A cylindrical battery was produced in the same manner as in Example II-19, for which, however, LiPF$_6$ to be 0.95 M and LiN(SO$_2$CF$_3$)$_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=23/5/2/50/20 as in Example II-19, and further, bis(2-vinylsulfonylethyl)ether was added thereto to prepare a nonaqueous electrolytic solution, in an amount of 1% by mass of the resulting nonaqueous electrolytic solution; and the battery was tested for the battery characteristics and the gas generation level. The results are shown in Table II-3.

TABLE II-2

| | Composition of Electrolyte Salt Composition of Nonaqueous Solvent (ratio by volume) | Sulfone Compound Type | Amount Added (% by mass) | Discharge Capacity Retention after 100 cycles (%) | Gas Generation (%) |
|---|---|---|---|---|---|
| Example II-10 | 1M LiPF6 EC/MEC/DEC (30/50/20) | bis(2-vinylsulfonylethyl) ether | 0.1 | 76 | 80 |
| Example II-11 | 1M LiPF6 EC/MEC/DEC (30/50/20) | bis(2-vinylsulfonylethyl) ether | 1 | 79 | 72 |
| Example II-12 | 1M LiPF6 EC/MEC/DEC (30/50/20) | bis(2-vinylsulfonylethyl) ether | 2 | 89 | 61 |
| Example II-13 | 1M LiPF6 EC/MEC/DEC (30/50/20) | bis(2-vinylsulfonylethyl) ether | 5 | 88 | 60 |
| Example II-14 | 1M LiPF6 EC/MEC/DEC (30/50/20) | bis(2-vinylsulfonylethyl) ether | 10 | 87 | 61 |
| Example II-15 | 1M LiPF6 EC/MEC/DEC (30/50/20) + ethylene sulfite: 0.5 wt % | bis(2-vinylsulfonylethyl) ether | 1 | 86 | 55 |
| Example II-16 | 1M LiPF6 EC/MEC/DEC(30/50/20) + 1,3-propanesultone: 2 wt % | bis(2-vinylsulfonylethyl) ether | 1 | 84 | 58 |
| Example II-17 | 0.95M LiPF6 + 0.05M LiTFSI EC/PC/VC/MEC/DEC (23/5/2/50/20) | bis(2-vinylsulfonylethyl) ether | 1 | 82 | 68 |
| Example II-18 | 0.95M LiPF6 + 0.05M LiBF4 FEC/PC/MEC/DEC (20/10/50/20) | bis(2-vinylsulfonylethyl) ether | 1 | 84 | 73 |
| Comparative Example II-4 | 1M LiPF6 EC/MEC/DEC (30/50/20) | none | — | 65 | 115 |

Comparative Example II-5

A cylindrical battery was produced in the same manner as in Example II-19, for which, however, $LiPF_6$ to be 0.95 M and $LiN(SO_2CF_3)_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=23/5/2/50/20 as in Example II-19, but 1,2-bis(vinylsulfonyl)ethane was not added thereto; and the battery was tested for the battery characteristics and the gas generation level. The results are shown in Table II-3.

and the gas generation level in the same manner as in Example II-1, for which, however, the final charging voltage was 3.6 V and the final discharging voltage was 2.0 V. The results are shown in Table II-4.

Example II-22

A cylindrical battery was produced in the same manner as in Example II-21, for which, however, $LiPF_6$ to be 0.95 M and $LiN(SO_2CF_3)_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=23/5/2/50/20, and further, bis(2-vinylsulfonylethyl)ether was added thereto to prepare a nonaqueous electrolytic solution, in an amount of 1% by mass of the resulting nonaqueous electrolytic solution; and the battery was tested for the battery characteristics and the gas generation level. The results are shown in Table II-4.

TABLE II-3

| | Composition of Electrolyte Salt | Sulfone Compound | | Discharge Capacity | Gas |
|---|---|---|---|---|---|
| | Composition of Nonaqueous Solvent (ratio by volume) | Type | Amount Added (% by mass) | Retention after 100 cycles (%) | Generation (%) |
| Example II-19 | 0.95M LiPF6 + 0.05M LiTFSI EC/PC/VC/MEC/DEC (23/5/2/50/20) | 1,2-bis(vinylsulfonyl) ethane | 1 | 65 | 72 |
| Example II-20 | 0.95M LiPF6 + 0.05M LiTFSI EC/PC/VC/MEC/DEC (23/5/2/50/20) | bis(2-vinylsulfonylethyl) ether | 1 | 68 | 66 |
| Comparative Example II-5 | 0.95M LiPF6 + 0.05M LiTFSI EC/PC/VC/MEC/DEC (23/5/2/50/20) | none | — | 23 | 114 |

Example II-21

A cylindrical battery was produced in the same manner as in Example II-1 except for the following: $LiFePO_4$ was used as the positive electrode active material in place of $LiCoO_2$. 90% by mass of $LiFePO_4$ (positive electrode active material), 5% by mass of acetylene black (electroconductive agent) and 5% by mass of polyvinylidene fluoride (binder) were mixed, to which was added a solvent of 1-methyl-2-pyrrolidone. The resulting mixture was applied onto an aluminium foil collector, dried, processed under pressure and cut into a predetermined size, thereby producing a long rectangular, positive electrode sheet. $LiPF_6$ to be 0.95 M and $LiN(SO_2CF_3)_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=23/5/2/50/20, and further 1,2-bis(vinylsulfonyl)ethane was added thereto to prepare a nonaqueous electrolytic solution, in an amount of 1% by mass of the resulting nonaqueous electrolytic solution. Thus produced, the battery was tested for the battery characteristics

Comparative Example II-6

A cylindrical battery was produced in the same manner as in Example II-21, for which, however, $LiPF_6$ to be 0.95 M and $LiN(SO_2CF_3)_2$ to be 0.05 M were dissolved in a nonaqueous solvent of ethylene carbonate (EC)/propylene carbonate (PC)/vinylene carbonate (VC)/methyl ethyl carbonate (MEC)/diethyl carbonate (DEC) (ratio by volume)=23/5/2/50/20, but 1,2-bis(vinylsulfonyl)ethane was not added thereto; and the battery was tested for the battery characteristics and the gas generation level. The results are shown in Table II-4.

TABLE II-4

| | Composition of Electrolyte Salt | Sulfone Compound | | Discharge Capacity | Gas |
|---|---|---|---|---|---|
| | Composition of Nonaqueous Solvent (ratio by volume) | Type | Amount Added (% by mass) | Retention after 100 cycles (%) | Generation (%) |
| Example II-21 | 0.95M LiPF6 + 0.05M LiTFSI EC/PC/VC/MEC/DEC (23/5/2/50/20) | 1,2-bis(vinylsulfonyl) ethane | 1 | 92 | 53 |
| Example II-22 | 0.95M LiPF6 + 0.05M LiTFSI EC/PC/VC/MEC/DEC (23/5/2/50/20) | bis(2-vinylsulfonylethyl) ether | 1 | 93 | 51 |
| Comparative Example II-6 | 0.95M LiPF6 + 0.05M LiTFSI EC/PC/VC/MEC/DEC (23/5/2/50/20) | none | — | 75 | 84 |

Example II-23

A cylindrical battery was produced in the same manner as in Example II-11, for which, however, 1,2,3-tris(vinylsulfonyl)propane was added to the non-aqueous electrolytic solution in an amount of 1% by mass of the solution, in place of adding bis(2-vinylsulfonylethyl)ether thereto; and the battery was tested for the battery characteristics and the gas generation level. As a result, the capacity retention after 100 cycles was 88%. The gas generation was 63%, based on the gas generation, 100% in Comparative Example II-1.

The lithium secondary batteries of Examples II-1 to II-18 and II-23 are all noticeably improved in point of the cycle property thereof, and especially the gas generation therein is significantly prevented, as compared with the lithium secondary batteries in Comparative Example II-1 where the sulfone compound having a vinyl group of the present invention was not added, Comparative Example II-2 where divinyl sulfone was added, and Comparative Example II-3 where 1,2-bis(methylsulfonyl)ethane was added. In addition, the battery in Comparative Example II-3 where 1,2-bis(methylsulfonyl)ethane was added could not produce any noticeable result in point of the cycle property and the gas generation-preventing effect thereof, as compared with the battery in Comparative Example II-1 where a sulfone compound was not added. Accordingly, it is known that, when a vinyl group-having sulfone compound of the present invention which has not only two or three sulfone groups but also two or three vinylsulfone groups in the molecule is added to a nonaqueous electrolytic solution of an electrolyte salt dissolved in a nonaqueous solvent, then it brings about unexpected specific effects.

From comparison between Examples II-19 and II-20 and Comparative Example II-5, and comparison between Examples II-21 and II-22 and Comparative Example II-6, the case where a lithium-containing olivine-type iron phosphate is used as the positive electrode, and the case where Si is used as the negative electrode also exhibit the same effects. Accordingly, it is obvious that the effects of the present invention do not depend on a specific positive electrode or negative electrode.

INDUSTRIAL APPLICABILITY

According to the present invention, there are provided novel sulfone compounds useful as intermediate materials for medicines, agricultural chemicals, electronic materials, polymer materials and the like, or as battery materials.

The lithium secondary battery using the nonaqueous electrolytic solution of the present invention is excellent in the battery characteristics such as the cycle property thereof, and releases little gas even when used at high temperatures. Therefore, the battery is free from a trouble of battery breakdown owing to its swelling or owing to a current shutdown mechanism acting on it, and can maintain the battery performance for a long period time.

The invention claimed is:

1. A nonaqueous electrolytic solution for lithium secondary batteries, comprising an electrolyte salt dissolved in a nonaqueous solvent and containing bis(2-propynyl)sulfone and/or a sulfone compound represented by formula (II) in an amount of from 0.01 to 10% by mass of the nonaqueous electrolytic solution:

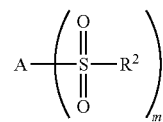

wherein $R^2$ represents a 2-propynyl group or a vinyl group; m is 2 or 3; A represents a divalent linking group having from 1 to 5 carbon atoms and optionally containing an ether bond when m is 2, but when m is 3, A represents a trivalent linking group composed of carbon and hydrogen atoms and having from 3 to 5 carbon atoms.

2. The nonaqueous electrolytic solution according to claim 1, wherein the nonaqueous solvent comprises a cyclic carbonate and a linear carbonate.

3. The nonaqueous electrolytic solution according to claim 2, wherein cyclic carbonate is at least one selected from the group consisting of ethylene carbonate, propylene carbonate, vinylene carbonate, 4-fluoro-1,3-dioxolan-2-one, trans-4,5-difluoro-1,3-dioxolan-2-one, and cis-4,5-difluoro-1,3-dioxolan-2-one.

4. The nonaqueous electrolytic solution according to claim 2, wherein the linear carbonate comprises a symmetric linear carbonate and an asymmetric linear carbonate.

5. The nonaqueous electrolytic solution according to claim 4, wherein the symmetric linear carbonate is one or more selected from the group consisting of dimethyl carbonate, diethyl carbonate, dipropyl carbonate, and dibutyl carbonate.

6. The nonaqueous electrolytic solution according to claim 4, wherein the asymmetric linear carbonate is one or more selected from the group consisting of methyl ethyl carbonate, methyl propyl carbonate, methyl isopropyl carbonate, methyl butyl carbonate, and ethyl propyl carbonate.

7. The nonaqueous electrolytic solution according to claim 1, wherein the electrolyte salt is one or more selected from the group consisting of $LiPF_6$, $LiBF_4$, $LiN(SO_2CF_3)_2$, and $LiN(SO_2C_2F_5)_2$.

8. The nonaqueous electrolytic solution according to claim 7, wherein the electrolyte salt comprises $LiPF_6$ in a molar ratio $LiPF_6/(LiBF_4$ or $LiN(SO_2CF_3)_2$ or $LiN(SO_2C_2F_5)_2)$ of from 70/30 to 99/1.

9. The nonaqueous electrolytic solution according to claim 1, wherein m is 2 and A represents a divalent linking group having from 1 to 5 carbon atoms and containing an ether bond.

10. The nonaqueous electrolytic solution according to claim 1, wherein the sulfone compound represented by formula (II) is one or more selected from the group consisting of bis(2-propynyl)sulfone, 1,2-bis(2-propynylsulfonyl)ethane, 1,3-bis(2-propynylsulfonyl)propane, 2,2'-bis(2-propynylsulfonylethyl)ether, bis(vinylsulfonyl)methane, 1,2-bis(vinylsulfonyl)ethane, 1,4-bis(vinylsulfonyl)butane, bis(2-vinylsulfonylethyl)ether, bis(vinylsulfonylpropyl)ether, and ethylene glycol bis(vinylsulfonylethyl)ether.

11. A lithium secondary battery comprising a positive electrode, a negative electrode and a nonaqueous electrolytic solution of an electrolyte salt dissolved in a nonaqueous solvent, wherein the nonaqueous electrolytic solution contains bis(2-propynyl)sulfone and/or a sulfone compound of formula (II) in an amount of from 0.01 to 10% by mass of the nonaqueous electrolytic solution:

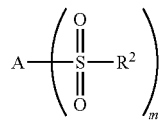 (II)

wherein $R^2$ represents a 2-propynyl group or a vinyl group, m is 2 or 3, and A represents a divalent linking group having from 1 to 5 carbon atoms and optionally containing an ether bond when m is 2, but when m is 3, A represents a trivalent linking group composed of carbon and hydrogen atoms and having from 3 to 5 carbon atoms.

12. The lithium secondary battery according to claim 11, wherein the positive electrode comprises a positive electrode active material comprising one or more selected from the group consisting of a lithium complex metal oxide and a lithium-containing olivine phosphate.

13. The lithium secondary battery according to claim 11, wherein the negative electrode comprises a negative electrode active material comprising one or more selected from the group consisting of lithium metal, a lithium alloy, a high-crystalline carbon material capable of absorbing and releasing lithium, and a metal compound capable of absorbing and releasing lithium.

* * * * *